United States Patent [19]

Horwell et al.

[11] Patent Number: 5,968,968
[45] Date of Patent: Oct. 19, 1999

[54] DIPHENYL-CYCLOPROPENES AS SELECTIVE K-AGONISTS

[75] Inventors: David C. Horwell, Cambridge; Verity Sabin, Cambridgeshire, both of United Kingdom

[73] Assignee: Warner-Lambert Company, Morris Plains, N.J.

[21] Appl. No.: 09/202,015

[22] PCT Filed: Jun. 18, 1997

[86] PCT No.: PCT/US97/10030

§ 371 Date: Dec. 8, 1998

§ 102(e) Date: Dec. 8, 1998

[87] PCT Pub. No.: WO98/03491

PCT Pub. Date: Jan. 29, 1999

Related U.S. Application Data

[60] Provisional application No. 60/022,336, Jul. 24, 1996.

[51] Int. Cl.$^6$ ................ A01N 43/56; C07D 207/06; C07D 207/08
[52] U.S. Cl. ................ 514/409; 514/429; 548/407; 548/578
[58] Field of Search ................ 548/407, 578; 514/429, 409

[56] References Cited

U.S. PATENT DOCUMENTS

| | | | |
|---|---|---|---|
| 5,116,842 | 5/1992 | Naylor et al. | 514/252 |
| 5,123,951 | 6/1992 | See et al. | 71/86 |
| 5,229,414 | 7/1993 | Main | 514/428 |
| 5,292,937 | 3/1994 | Manning et al. | 562/457 |

OTHER PUBLICATIONS

H. Rogers et al., "GR94839, a –opoid agoinst with limited access to the central nervous system, has antinociceptive activity", Br. J. Pharmocol., vol. 106, pp. 783–789, 1992.

Bushby et al., The Attempted Generation of . . ., J. Chem. Res., Synop., 4, pp. 126–127. Dec. 1986.

Neunhoeffer et al., "Synthese von 1,2,3,–Triazincarbonsäureestern", Liebigs Ann. Chem., vol. 4, 1993, pp. 367–373 Oct. 1992.

Breslow and Battistle, "Detection of a cyclopropenyl anion by deuterium exchange", Chem. & Ind. (London), 1958, pp. 1143–1144.

Bushby and Jesudason, "The Attempted Generation of a Methylene–bridged Trimethylenemethane Biradical (1,3–Diphenyl–2–methylenecyclobutane–1,3–diyl) by Oxidation of endo–1,3–Diphenyl1–2(phenylselenomethyl)–bicyclobutane", J. Chem. Res. Synop., vol. 4, 1986, pp. 126–127.

Donaldson and Hughes, "Mechanism of Formation of (?$^3$–Oxocyclobutenyl)cobalt Compounds from [Co(CO)$_4$]$^-$ and Cyclopenium Cations", J. Am. Chem. Soc., vol. 104, No. 18, 1982, pp. 4846–4859.

White et al., "Versuche zur Dartstellung vin Diphenyltetrahedron", Chem. Ber., vol. 114, No. 12, 1981, pp. 3906–3915.

Farid and Brown, "Exciplex Formation and Electron–transfer in the Photoreaction of 9,10–Dicyanoanthracene and Methyl 1,2–Diphenylcyclopropene–3–carboxylate", J.C.S. Chem. Comm., vol. 14, 1976, pp. 564–565.

D'yankonov et al., "1,3–dipolar addition" of carbethoxycarbene to the acetylenic bond and a new isomerization in the cyclopropene field, Zh. Org. Khim., vol. 5, No. 10, 1969, pp. 1689–1692.

Breslow and Douek, "Antiaromatic Effects in Cyanocyclopropenyl Anions", J. Am. Chem. Soc., vol. 90, No. 10, 1968, pp. 2968–2699.

Jones et al., "Attempts to Generate Diphenylcyclopropenylidene. IV", J. Am. Chem. Soc., vol. 90, No. 7, 1968, pp. 1849–1859.

Shono et al., "A Novel Base Useful for Synthesis of Esters and Macrolides", J. Org. Chem., vol. 51, No. 4, 1986, pp. 546–549.

Hughes and Robinson, "Transition–Metal–Promoted Activation of Carbon–Carbon Bonds. A New Synthetic Route to Substituted Ruthenocene Derivatives via Ring Expansion Reactions of 3–Vinyl–1–cyclopropenes", Organometallics, vol. 8, No. 4, 1989, pp. 1015–1019.

Castellucci et al., "Photolysis of 2,3–Diphenylcycloprop–2–enecarboxylic Acid Azide and its Homologue", Chem. Commun., vol. 10, 1967, pp. 473–474.

Domnin et al., "Main Fragmentation Routes of Functionally Substituted Cyclopropenes Under Electron Impact", Org. Mass. Spectrom., Vol. 20, No. 1, 1985, pp. 674–676.

Blatchford and Orchin, "The Synthesis of Some 2,3–Diarylcyclopropane–1–carboxylic Acids", J. Org. Chem., Vol. 29, No. 4, 1964, pp. 839–843.

D'yakonov and Komendantov, "Reactions of aliphatic diazo compounds with unsaturated compounds. XXIII. Reaction of ethyl diazoacetate with diphenylacetylene", Zh. Obshch. Khim., Vol. 33, No. 8, 1963, pp. 2448–2456.

Flowers and Frey, "The Thermal Isomerization of 1,1–Dimethylcyclopropane", J. Chem Soc., 1959, pp. 3953–3957.

Breslow et al., "On Darling's Cyclopropene Derivative and Its Rearrangement", J. Org. Chem., Vol. 24, 1959, pp. 415–416.

Primary Examiner—Robert W. Ramsuer
Assistant Examiner—Dominic Keating
Attorney, Agent, or Firm—Elizabeth M. Anderson

[57] ABSTRACT

Diphenyl-cyclopropene derivatives, their nontoxic, pharmaceutically acceptable acid addition salts and compositions are kapa opiods useful in the treatment of pain, inflammation, Parkinsonism, dystonia, cerebral ischemia, diuresis, asthma, psoriasis, irritable bowel syndrome and stroke.

12 Claims, No Drawings

DIPHENYL-CYCLOPROPENES AS SELECTIVE K-AGONISTS

This Application is a 371 of PCT/U.S. 97/10030, Filed Jun. 18, 1997, which claims the Benefit of U.S. Provisional Application Ser. No. 60/022,336, Filed Jul. 24, 1996.

BACKGROUND OF THE INVENTION

The diphenyl-cyclopropene derivatives of the instant invention are kappa opioids useful in the treatment of pain, inflammation, Parkinsonism, dystonia, cerebral ischemia, diuresis, asthma, psoriasis, irritable bowel syndrome, and stroke.

The compounds are K-agonists which are centrally acting and peripherally selective acting.

SUMMARY OF THE INVENTION

The instant invention is a compound of Formula I

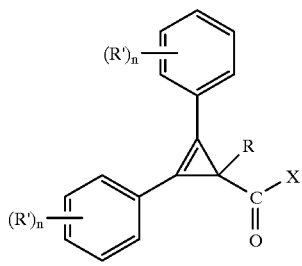

or a pharmaceutically acceptable salt thereof wherein x is

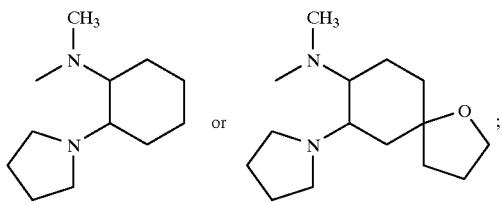

n is an integer of from 0 to 4; and

R' is halogen, $CF_3$, $NO_2$, $OR^2$, $CONR^3R^4$, or $NHCOCH_3$ wherein $R^2$, $R^3$, and $R^4$ are each independently selected from hydrogen and alkyl of from 1 to 6 carbons.

R is hydrogen, COOH, or $COOCH_3$.

Particularly useful are the compounds selected from:

2,3-Diphenyl-cycloprop-2-enecarboxylic acid methyl-(2-pyrrolidin-1-yl-cyclohexyl)-amide;

2,3-Diphenyl-cycloprop-2-enecarboxylic acid methyl-(7-pyrrolidin-1-yl-1-oxa-spiro[4.5]dec-8-yl)-amide;

Ethyl 2-(3-chlorophenyl)-3-phenylcycloprop-2-ene-1-carboxylate;

2-(3-Chlorophenyl)-3-phenyl-cycloprop-2-ene-1-carboxylic acid;

2-(3-Chlorophenyl)-3-phenyl-cycloprop-2-enecarboxylic acid methyl-(2-pyrrolidin-1-yl-cyclohexyl)-amide;

Ethyl 2-(4-chlorophenyl)-3-phenyl-cycloprop-2-ene-1-carboxylate;

2-(4-Chlorophenyl)-3-phenyl-cycloprop-2-ene-1-carboxylic acid;

2-(4-Chlorophenyl)-3-phenyl-cycloprop-2-enecarboxylic acid methyl-(2-pyrrolidin-1-yl-cyclohexyl)-amide;

1-[Methyl-(2-pyrrolidin-1-yl-cyclohexyl)-carbamoyl]-2,3-diphenyl-cycloprop-2-enecarboxylic acid methyl ester; and 1-[Methyl-(2-pyrrolidin-1-yl-cyclohexyl)-carbamoyl]-2,3-diphenyl-cycloprop-2-enecarboxylic acid.

DETAILED DESCRIPTION

In the compounds of Formula I above, the phenyl groups may be unsubstituted or substituted by 1 to 3 substituents each independently selected from halogen, $CF_3$, $NO_2$, $OR^2$, $CONR^3R^4$ wherein $R^2$, $R^3$, and $R^4$ are each independently hydrogen or alkyl with from 1 to 6 carbons, and $NHCOCH_3$. Preferred substituents are halogens, especially a monochloro group.

Compounds of the present invention contain one or more asymmetric carbon atoms and therefore exist in various stereoisomeric forms. Additionally, the compounds of this invention exist in different geometric isomeric forms. The instant invention is all geometric and stereoisomeric forms.

The compounds of the present invention and/or their nontoxic, pharmaceutically acceptable acid addition salts may be administered to mammals in pharmaceutical compositions which comprise one or more compounds of this invention and/or salts thereof in combination with a pharmaceutically acceptable nontoxic carrier.

As parenteral compositions, the compounds of this invention may be administered with conventional injectable liquid carriers such as sterile, pyrogen-free water, sterile peroxide-free ethyl oleate, dehydrated alcohols, polypropylene glycol, and mixtures thereof Suitable pharmaceutical adjuvants for the injectable solutions include stabilizing agents, solubilizing agents, buffers, and viscosity regulators. Examples of these adjuvants include ethanol, ethylenediamine tetraacetic acid (EDTA), tartrate buffers, citrate buffers, and high molecular weight polyethylene oxide viscosity regulators. These pharmaceutical formulations may be injected intramuscularly, intraperitoneally, or intravenously.

As solid or liquid pharmaceutical compositions, the compounds of the present invention may be administered to mammals orally in combination with conventional compatible carriers in solid or liquid form. These orally administered pharmaceutical compositions may contain conventional ingredients such as binding agents such as syrups, acacia, gelatin, sorbitol, tragacanth, polyvinylpyrrolidone, and mixtures thereof.

The compositions may further include fillers such as lactose, mannitol, starch, calcium phosphate, sorbitol, methylcellulose, and mixtures thereof.

These oral compositions may also contain lubricants such as magnesium stearate, high molecular weight polymers such as polyethylene glycol, high molecular weight fatty acids such as stearic acid, silica, or agents to facilitate disintegration of the solid formulation such as starch, and wetting agents such as sodium lauryl sulfate.

The oral pharmaceutical compositions may take any convenient form such as tablets, capsules, lozenges, aqueous or oily suspensions, emulsions, or even dry powders which may be reconstituted with water or other suitable liquids prior to use.

The solid or liquid forms may contain flavorants, sweeteners, and/or preservatives such as alkyl p-hydroxybenzoates. The liquid forms may further contain suspending agents such as sorbitol, glucose, or other sugar syrups, methyl-, hydroxymethyl-, or carboxymethylcellulose, and gelatin, emulsifying agents such as lecithin or sorbitol monooleate, and conventional thickening agents. The liquid compositions may be encapsulated in, for example, gelatin capsules.

As topically administered pharmaceutical compositions, the compounds of the present invention may be administered in the form of ointments or creams containing from about 0.1% to about 10% by weight of the active component in a pharmaceutical ointment or cream base.

Compounds of the present invention may be rectally administered in the form of suppositories. For preparing suppositories, a low-melting wax such as a mixture of fatty acid glycerides or cocoa butter is first melted and the active ingredient is dispersed homogeneously in the melt. The mixture is then poured into convenient sized molds and allowed to cool and solidify.

Preferably, the pharmaceutical compositions of this invention are in unit dosage form. In such form, the preparation is subdivided into unit doses containing appropriate amounts of the active component. The unit dosage can be a packaged preparation with the package containing discrete quantities of the preparation. For example, the package may take the form of packaged tablets, capsules, and powders in envelopes, vials, or ampoules. The unit dosage form can also be a capsule, cachet, or tablet itself or can be the appropriate number of any of these packaged forms The quantity of active compound in the unit dosage form may be varied or adjusted from about 0.5 mg to about 350 mg according to the particular application and the potency of the active ingredient.

When employed systematically in therapeutic use as analgesic agents in the pharmaceutical method of this invention, the compounds are administered at doses of from about 0.05 mg to about 2.0 mg of active compound per kilogram of body weight of the recipient.

The rabbit vas deferens is a specific test for activity at the K-receptor and allows comparison of potency and efficacy of a test ligand and its parent K-agonist. Rabbit vas deferens assay (Oka T., Negiski K., et al., *Eur. J. Pharmacol.*, 1981;73:235) was used to test the compounds of the invention. One of the compounds of the invention, the compound of Example 4, 2,3-Diphenyl-cycloprop-2-enecarboxylic acid methyl-(7-pyrrolidin-1-yl-1-oxa-spiro[4.5]dec-8-yl)-amide, exhibited agonist functional activity of $EC_{50}(LID)=$ 12 nM.

Example 14 has a carboxylic acid moiety that is likely to confer peripherally active properties to such compounds. The advantage of a peripherally selective K-agonist is that it should be free of CNS-mediated effects on mood, cognition, and motor function but still retain analgesic properties against inflammatory pain of peripheral origin. Hence both centrally acting and peripherally selective actions contribute an embodiment of this invention.

The following specific preparative examples are provided to enable one skilled in the art to practice the present invention. These examples are not to be read as limiting the scope of the invention as defined by the appended claims, but merely as illustrative thereof.

EXAMPLE 1

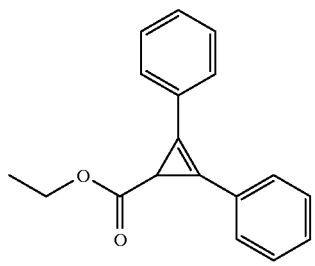

Ethyl 2,2-diphenyl-cycloprop-2-ene-1-carboxylate

Ethyl diazoacetate (0.6 cm$^3$, 5.7 mmol) in dichloromethane (5 cm$^3$) was added dropwise to a solution of diphenylacetylene in dichloromethane (9 cm$^3$), containing a catalytic quantity of rhodium acetate dimer, at 45° C. under nitrogen. Upon completion of addition, the mixture was cooled to room temperature and the solvent evaporated. The residue was chromatographed (SiO$_2$, 20% dichloromethane in heptane to elute unreacted diphenylacetylene followed by 1:1 dichloromethane/heptane) to separate the cyclopropene ester 0.26 g, 15%.

$R_f$=0.39 (SiO$_2$, 2:1 heptane/ethyl acetate). $v_{max}$/cm$^{-1}$ 2980 (C—H) and 1723 (C=O). $^1$HNMR (400 mHz, CDCl$_3$) 7.70–7.68 (4H, m), 7.50–7.46 (4H, m), 7.41–7.37 (2H, m), 4.20 (2H, q, J =7.2, OCH$_2$CH$_3$), 2.82 (H, s, CHCO$_2$), and 1.24 (3H, t, J =7.2, OCH$_2$CH$_3$).

EXAMPLE 2

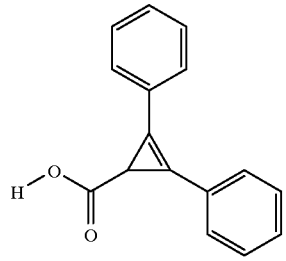

2,3-Diphenyl-cycloprop-2-ene-1-carboxylic acid

Ethyl 2,3-diphenyl-cycloprop-2-ene-1-carboxylate (1.75 g, 6.6 mol) and potassium hydroxide (1.79 g, 31.9 mmol) were dissolved in methanol (60 cm$^3$) and heated to reflux for 5 hours. The mixture was cooled to room temperature and the solvent evaporated. The residue was partitioned between water (30 cm$^3$) and ethyl acetate (30 cm$^3$) The aqueous layer was separated and washed with ethyl acetate (2×30 cm$^3$) before being acidified to pH=1 with dilute hydrochloric acid and extracted with dichloromethane (3×40 cm$^3$). The combined dichloromethane extracts were dried (MgSO$_4$) and evaporated to give the cyclopropene acid 1.22 g, 78%.

$v_{max}$/cm$^{-1}$ 1687 (C=O).

$^1$HNMR (400 mHz, CDCl$_3$): 7.72–7.69 (4H, m), 7.51–7.42 (4H, m), 7.39–7.35 (2H, m), and 2.83 (H, s, CHCO$_2$).

EXAMPLE 3

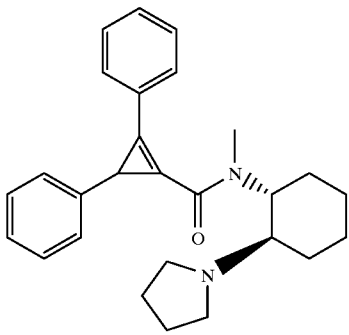

2,3-Diphenyl-cycloprop-2-ene-1-carboxylic acid methyl-(2-pyrrolidin-1-yl-cyclohexyl)-amide 2,3-Diphenyl-cycloprop-2-ene-1-carboxylic acid (0.34 g, 1.44 mmol) was dissolved in chloroform (6.0 cm$^3$). Thionyl chloride (0.42 cm$^3$, 5.80 mmol) was added and the mixture stirred at room temperature for 2 days. The mixture was evaporated to dryness and the residue examined by IR, which showed $v_{max}$ at 1770 cm$^{-1}$, indicating that the carboxylic acid group had been completely converted to an acid chloride. The crude acid chloride was dissolved in dichloromethane (3 cm$^3$) and added dropwise to a solution of trans N-methyl-N-2-(1-pyrrolidinyl)cyclohexylamine (0.26 g, 1.44 mmol) in dichloromethane (4 cm$^3$) cooled in an ice bath under nitrogen. The mixture was stirred at room temperature for 30 minutes and then evaporated to give the amine hydrochloride 0.27 g, 43%; mp 175–178° C. (from ether-dichloromethane). $v_{max}$/cm$^{-1}$ 1631 (C═O).

Analysis for $C_{27}H_{32}N_2O$ .HCl .H$_2$O: Requires: C, 71.29; H, 7.70; N, 6.16. Found: C, 71.54; H, 7.56; N, 6.23.

$^1$HNMR (400 mHz, CDCl$_3$): 7.87–7.85 (2H, m), 7.64–7.62 (2H, m), 7.48–7.43 (4H, m), 7.38–7.34 (2H, m), 3.80 (H, br s), 2.26–2.23 (H, m), 2.18–2.00 (2H, br m), 1.85–1.56 (7H, m), 1.58–1.54 (H, m), and 1.38–1.22 (2H, m).

100% by HPLC; retention time =16.97 minutes (10% to 80% MeCN in H$_2$O+1% TFA over 20 minutes).

EXAMPLE 4

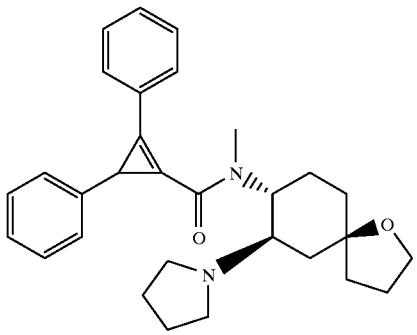

2,3-Diphenyl-cycloprop-2-ene-1-carboxylic acid methyl-(7-pyrrolidin-1-yl-1-oxa-spiro[4.5]dec-8-yl)-amide 2,3-Diphenyl-cycloprop-2-ene-1-carboxylic acid (1.22 g 5.17 mmol) was dissolved in dichloromethane (20 cm$^3$). Thionyl chloride (1.50 cm$^3$, 20.68 mmol) was added and the mixture stirred at room temperature for 2 days. The mixture was evaporated to dryness and the residue examined by IR, which showed $v_{max}$ at 1769 cm$^{-1}$, indicating that the carboxylic acid group had been completely converted to an acid chloride. The crude acid chloride was dissolved in dichloromethane (15 cm$^3$) and added dropwise to a solution of N-methyl-7-(1-pyrrolidinyl)-1-oxa-spiro[4.5]decanamine (1.40 g, 5.17 mmol) in dichloromethane (10 cm$^3$) cooled in an ice bath under N$_2$. The mixture was stirred at room temperature for 30 minutes and then evaporated to give the amine hydrochloride. It was washed with ether, stirred with ethanolic ammonia (10 cm$^3$) for 30 minutes and then evaporated. The residue was chromatographed (SiO$_2$, 1% to 5% methanol in dichloromethane) to separate the major UV-active component (R$_f$=0.53 [SiO$_2$, 10% methanol in dichloromethane]) which was dissolved in methanol (5 cm$^3$) and hydrogen chloride (1.0 cm$^3$ of a 4.0 mol dm$^{-3}$ solution in dioxane) added. The mixture was stirred for 10 minutes at room temperature, evaporated, washed with ether, and dried in vacuo to give the amine hydrochloride 0.15 g, 6%; mp 148–150° C. $v_{max}$/cm$^{-1}$ 1634 (C═O).

Analysis for $C_{30}H_{36}N_2O_2$.(HCl)$_2$ .H$_2$O: Requires: C, 70.51; H, 7.64; N, 5.48. Found: C, 70.20; H, 7.50; N, 5.35.

$^1$HNMR (400 mHz, CDCl$_3$). 7.86–7.46 (2H, m), 7.64–7.63 (2H, m), 7.48–7.43 (4H, m), 7.38–7.34 (2H, m), 3.85–3.32 (2H, m, OCH$_2$), 3.57 (3H, br s, NCH$_3$), 3.19 (H, s, CHCO), 3.00 (H, br s), 2.80 (H, br s), and 2.13–1.64 (18H, m).

100% by HPLC; retention time =15.52 minutes (20% to 80% MeCN in H$_2$O+1% TFA over 20 minutes).

EXAMPLE 5

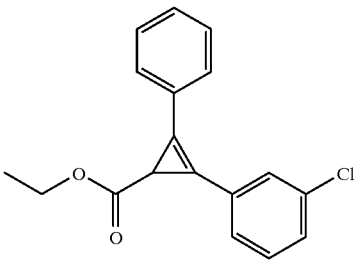

Ethyl 2-(3-chlorophenyl)-3-phenyl-cycloprop-2-ene-1-carboxylate

Ethyl diazoacetate (0.2 cm$^3$, 1.9 mmol) in dichloromethane (8 cm$^3$) was added dropwise to a solution of 1-(3-chlorophenyl)-2-phenylacetylene (1.7 g, 8.0 mmol) in dichloromethane (3 cm$^3$) containing a catalytic quantity of rhodium acetate dimer at 40° C. under nitrogen. Upon completion of addition, the mixture was heated at 40° C. for a further 15 minutes, then cooled to room temperature and the solvent evaporated. The residue was chromatographed (SiO$_2$, 5% dichloromethane in heptane to elute unreacted acetylene followed by 25% dichloromethane in heptane) to separate the cyclopropene ester. The unreacted acetylene was recycled, using further portions of ethyl diazoacetate (each 1.9 mmol) to give (after four repetitions) the cyclopropene ester 0.55 g, 24%.

R$_f$=0.33 (SiO$_2$, 6:1 heptane/dichloromethane).

$v_{max}$/cm$^{-1}$ 1728 (C═O).

$^1$HNMR (400 mHz, CDCl$_3$): 7.68–7.64 (3H, m), 7.57–7.55 (H, m), 7.50–7.47 (2H, m), 7.43–7.37 (3H, m), 4.18 (2H, q, J =7.2, OCH$_2$CH$_3$), 2.82 (H, s, CHCO$_2$), and 1.55 (3H, t, J =7.2, OCH$_2$CH$_3$).

EXAMPLE 6

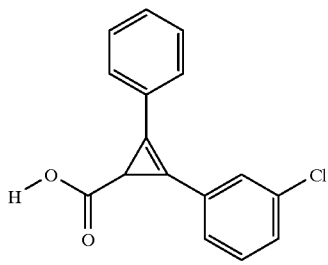

2-(3-Chlorophenyl)-3-phenyl-cycloprop-2-ene-1-carboxylic acid

Ethyl 2-(3-chloro-phenyl)-3-phenyl-cycloprop-2-ene-1-carboxylate (0.55 g, 1.84 mmol) and potassium hydroxide (0.5 g, 9.25 mmol) were dissolved in methanol (20 cm³) and heated to reflux for 2 hours. The mixture was cooled to room temperature and the solvent evaporated. The residue was partitioned between water (30 cm³) and ethyl acetate (30 cm³). The aqueous layer was separated and washed with ethyl acetate (2×30 cm³) before being acidified to pH =1 with dilute hydrochloric acid and extracted with dichloromethane (3×40 cm³). The combined dichloromethane extracts were dried (MgSO₄), evaporated, and washed with heptane to give the cyclopropene acid 0.21 g, 42%.

$v_{max}$/cm$^{-1}$ 1680 (C=O).

¹HNMR (400 mHz, CDCl₃): 7.70–7.65 (3H, m), 7.58–7.56 (H, m), 7.52–7.49 (2H, m), 7.44–7.36 (3H, m), and 2.82 (H, s, CHCO₂).

EXAMPLE 7

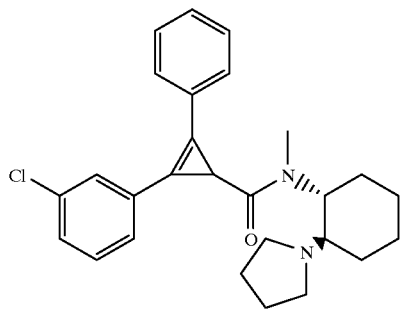

2-(3-Chlorophenyl)-3-phenyl-cycloprop-2-ene-1-carboxylic acid methyl-(2-pyrrolidin-1-yl-cyclohexyl)-amide 2-(3-Chlorophenyl)-3-phenyl-cycloprop-2-ene-1-carboxylic acid (0.2 g, 0.74 mmol) was dissolved in chloroform (3 cm³). Thionyl chloride (0.28 cm³, 3.80 mmol) was added and the mixture stirred at room temperature for 2 days. The mixture was evaporated to dryness and the residue examined by IR, which showed $v_{max}$ at 1770 cm$^{-1}$, indicating that the carboxylic acid group had been completely converted to an acid chloride. The crude acid chloride was dissolved in dichloromethane (2 cm³) and added dropwise to a solution of N-methyl-N-2-(1-pyrrolidinyl)-cyclohexylamine (0.14 g, 0.74 mmol) in dichloromethane (3 cm³) cooled in an ice bath under N₂. The mixture was stirred at room temperature for 30 minutes and then evaporated to give the amine hydrochloride 0.065 g, 14%; mp 247–249° C. (from ether-dichloromethane).

$v_{max}$/cm$^{-1}$ 1634 (C=O). Analysis for $C_{27}H_{31}ClN_2O\cdot HCl\cdot(H_2O)_{1.5}$: Requires: C, 65.00; H, 7.03; N, 5.62. Found: C, 64.77; H, 6.56; N, 5.57.

¹HNMR (400 mHz, CDCl₃): 7.86 (2H, br s), 7.62–7.59 (2H, m), 7.54–7.31 (5H, m), 3.86 (H, br s), 3.55 (4H, br s, NCH₃ +CH), 3.26 (H, s, CHCO), 3.15 (H, br s), 2.84 (H, br s), 2.24–2.08 (3H, br m), 1.96–1.44 (9H, m), and 1.40–1.26 (2H, m).

100% by HPLC; retention time =18.04 minutes (20% to 80% MeCN in H₂O +1% TFA over 20 minutes).

EXAMPLE 8

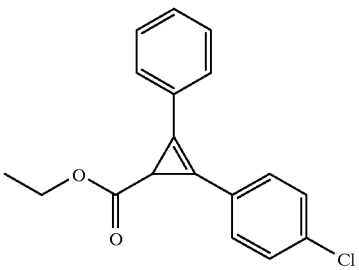

Ethyl 2-(4-chlorophenyl)-3-phenyl-cycloprop-2-ene-1-carboxylate

Ethyl diazoacetate (0.34 cm³, 3.3 mmol) in dichloromethane (7 cm³) was added dropwise to a solution of 1-(4-chlorophenyl)-2-phenylacetylene (2.76 g, 13.0 mmol) in dichloromethane (4 cm³) containing a catalytic quantity of rhodium acetate dimer at 40° C. under nitrogen. Upon completion of addition, the mixture was heated at 40° C. for a further 15 minutes, then cooled to room temperature and the solvent evaporated. The residue was chromatographed (SiO₂, 7% dichloromethane in heptane to elute unreacted acetylene followed by 1:1 dichloromethane/heptane) to separate the cyclopropene ester. The unreacted acetylene was recycled, using further portions of ethyl diazoacetate (each 3.3 mmol) to give (after three repetitions) the cyclopropene ester 0.66 g, 22%.

$R_f$=0.33 (SiO₂, 6:1 heptane/ethyl acetate).

$v_{max}$cm$^{-1}$ 1728 (C=O).

¹HNMR (400 mHz, CDCl₃): 7.65 (2H, dd, J =1.2 and 8.4), 7.59 (2H, dd, J =2.0 and 6.4), 7.49 (5H, m), 4.19 (2H, q, J =7.2, OCH₂CH₃), 2.81 (H, s, CHCO₂), and 1.24 ( H, t, J =7.2, OCH₂CH₃).

EXAMPLE 9

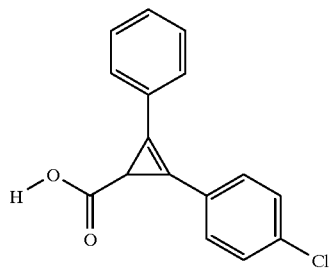

2-(4-Chlorophenyl)-3-phenyl-cycloprop-2-ene-1-carboxylic acid

Ethyl 2-(4-chlorophenyl)-3-phenyl-cycloprop-2-ene-1-carboxylate (0.66 g, 2.20 mmol) and potassium hydroxide (0.7 g, 12.95 mmol) were dissolved in methanol (25 cm³) and heated to reflux for 2 hours. The mixture was cooled to room temperature and the solvent evaporated. The residue was partitioned between water (30 cm³) and ethyl acetate (30 cm³). The aqueous layer was separated and washed with ethyl acetate (2×30 cm³) before being acidified to pH=1 with dilute hydrochloric acid and extracted with dichloromethane (3×40 cm³). The combined dichloromethane extracts were dried (MgSO₄), evaporated and washed with heptane to give the cyclopropene acid 0.27 g, 45%.

$v_{max}$/cm⁻¹ 1678 (C=O).

¹HNMR (400 mHz, CDCl₃): 7.69 (2H, m), 7.63–7.60 (2H, m), 7.52–7.40 (5H, m), and 2.81 (H, s, CHCO₂).

EXAMPLE 10

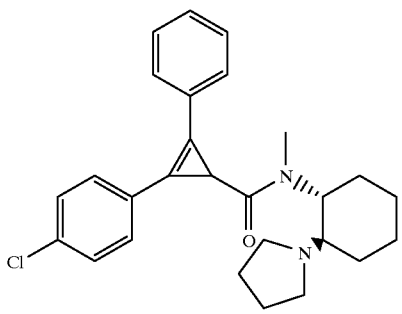

2-(4-Chlorophenyl)-3-phenyl-cycloprop-2-ene-1-carboxylic acid methyl-(2-pyrrolidin-1-yl-cyclohexyl)-amide 2-(4-Chlorophenyl)-3-phenyl-cycloprop-2-ene-1-carboxylic acid (0.25 g, 0.92 mmol) was dissolved in chloroform (3.0 cm³). Thionyl chloride (0.28 cm³, 3.80 mmol) was added and the mixture stirred at room temperature for 2 days. The mixture was evaporated to dryness and the residue examined by IR, which showed $v_{max}$ at 1770 cm⁻¹, indicating that the carboxylic acid group had been completely converted to an acid chloride. The crude acid chloride was dissolved in dichloromethane (2 cm³) and added dropwise to a solution of N-methyl-N-2-(1-pyrrolidinyl)-cyclohexylamine (0.17 g, 0.92 mmol) in dichloromethane (4 cm³) cooled in an ice bath under nitrogen. The mixture was stirred at room temperature for 30 minutes and then evaporated to give the amine hydrochloride 0.145 g, 33%; mp 252–254° C. (from ether-dichloromethane).

$v_{max}$/cm⁻¹ 1634 (C=O).

Analysis for C₂₇H₃₁ClN₂O .HCl.(H₂O)₀.₂₅: Requires: C, 68.14; H, 6.83; N, 5.89. Found: C, 68.12; H, 6.81; N, 5.90.

¹HNMR (400 mHz, CDCl₃): 8.99–7.92 (2H, br m), 7.60–7.58 (2H, m), 7.46–7.38 (4H, m), 7.36–7.34 (H, m), 3.90 (H, br s), 3.54 (3H, s, NCH₃), 3.25 (H, s, CHCO), 3.02 (H, br s), 2.86 (H, br s), 2.17–2.00 (3H, m), and 1.88–1.28 (12H, m).

100% by HPLC; retention time =18.03 minutes (20% to 80% MeCN in H₂O +1% TFA over 20 minutes).

EXAMPLE 11

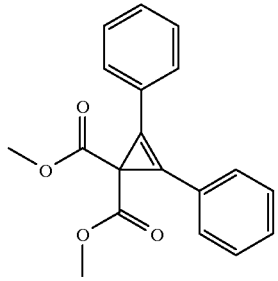

Dimethyl 2,3-diphenyl-cycloprop-2-ene-1,1-dicarboxylate

A mixture of diphenylacetylene (12.4 g, 69.7 mmol) and catalytic copper (II) acetylacetonate was heated to 145° C. under nitrogen. Diazodimethylmalonate (2.2 g, 13.9 mmol) was added dropwise. The mixture was heated at 145° C. for a further 30 minutes after completion of addition. It was cooled to room temperature and chromatographed (SiO₂, 20% dichloromethane in heptane to elute unreacted diphenylacetylene followed by 1:1 dichloromethane/heptane) to give the cyclopropene diester 0.63 g, 15%.

$R_f$=0.59 (SiO₂, 1:1 heptane/ethyl acetate).
$v_{max}$/cm⁻¹ 1755 (C=O).
¹HNMR (400 mHz, CDCl₃): 7.78–7.73 (4H, m), 7.52–7.41 (6H, m), and 3.73 (6H, s, OCH₃).

EXAMPLE 12

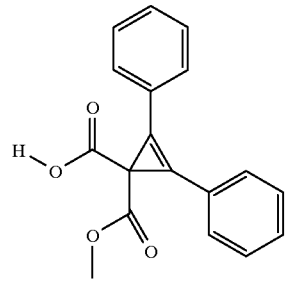

Methyl 2,3-diphenyl-cycloprop-2-ene-1-carboxylate-1-carboxylic acid

Dimethyl 2,3-diphenyl-cycloprop-2-ene-1,1-dicarboxylate (0.61 g, 2.00 mmol) and lithium hydroxide (0.082 g, 2.00 mmol) were dissolved in a mixture of methanol (10 cm³) and dichloromethane (6 cm³). The mixture was heated to reflux for 2 hours, cooled to room temperature, and the solvents evaporated. The residue was partitioned between water (20 cm³) and ethyl acetate (20 cm³). The aqueous layer was separated and washed with ethyl acetate (2×20 cm³) before being acidified to pH=1 with dilute hydrochloric acid and extracted with dichloromethane (3×25 cm³). The combined dichloromethane extracts were dried (MgSO₄), evaporated, and chromatographed (SiO₂, dichloromethane followed by 1% methanol in dichloromethane) to give the cyclopropene monoacid 0.22 g, 58%.

$R_f$=0.17 (SiO₂, 1:1 heptane/ethyl acetate).
$v_{max}$/cm⁻¹ 1732 (C=O ester) and 1694 (C=O acid).
¹HNMR (400 mHz, CDCl₃): 7.64–7.61 (4H, m), 7.53–7.43 (6H, m), and 3.71 (3H, s, OCH₃).

EXAMPLE 13

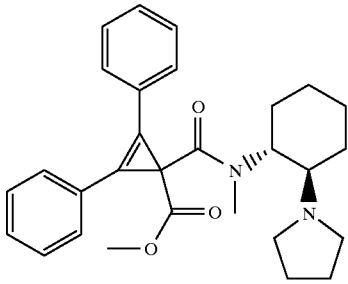

1-[Methyl-(2-pyrrolidin-1-yl-cyclohexyl)-carbamoyl]-2,3-diphenyl-cycloprop-2-enecarboxylic acid methyl ester Methyl 2,3-diphenyl-cycloprop-2-ene-1-carboxylate-1-carboxylic acid (0.21 g, 0.71 mmol) was dissolved in chloroform (4.0 cm$^3$). Thionyl chloride (0.21 cm$^3$, 2.85 mmol) was added and the mixture stirred at room temperature for 2 days. The mixture was evaporated to dryness and the residue examined by IR, which showed $v_{max}$ at 1778 and 1733 cm$^{-1}$, indicating that the carboxylic acid group had been completely converted to an acid chloride. The crude acid chloride was dissolved in dichloromethane (2 cm$^3$) and added dropwise to a solution of N-methyl-N-2-(1-pyrrolidinyl)-cyclohexylamine (0.13 g, 0.71 mmol) in dichloromethane (3 cm$^3$) cooled in an ice bath under nitrogen. The mixture was stirred at room temperature for 30 minutes and then evaporated to dryness. The residue was dissolved in ethanolic ammonia for 30 minutes at room temperature and the solvent evaporated. The residue was partitioned between water (10 cm$^3$) and dichloromethane (10 cm$^3$). The organic layer was washed with water (3×10 cm$^3$), dried, and evaporated to give the amine. Half the material was chromatographed (SiO$_2$, 5% methanol in dichloromethane) to separate the major UV-active component ($R_f$=0.42 [SiO$_2$, 10% methanol in dichloromethane]). It was dissolved in methanol (2.0 cm$^3$), hydrogen chloride (1.0 cm$^3$ of a 4.0 mol dn$^{-3}$ solution in dioxane) was added, and the mixture was stirred at room temperature for 30 minutes. The solvents were evaporated and the residue washed with ether and dried in vacuo to give the amine hydrochloride 0.097 g, 53%; mp 112–114° C.

$v_{max}$/cm$^{-1}$ 1716 (OC=O) and 1634 (NC=O).

Analysis for $C_{29}H_{34}N_2O_3$.HCl.H$_2$O: Requires: C, 65.60; H, 7.35; N, 5.28. Found: C, 65.45; H, 7.24; N, 5.18.

$^1$HNMR (400 mHz, CDCl$_3$): 7.76–7.70 (4H, m), 6.52–7.43 (6H, m), 3.96 (H, br s), 3.73 (3H, s, OCH$_3$), 3.60 (H, br s), 3.50 (H, br s), 3.36 (3H, s, NCH$_3$), 2.88 (H, br s), 2.74 (H, br s), 2.37 (H, br s), 1.96–1.52 (9H, m), and 1.37–1.20 (3H, m).

100% by HPLC; retention time =18.69 minutes (20% to 80% MeCN in H$_2$O +1% TFA over 20 minutes).

EXAMPLE 14

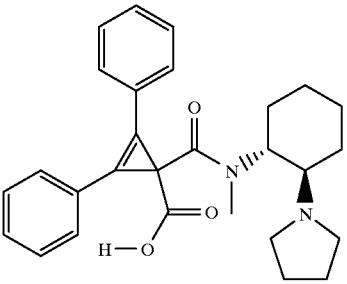

1-[Methyl-(2-pyrrolidin-1-yl-cyclohexyl)-carbamoyl]-2,3-diphenyl-cycloprop-2-enecarboxylic acid A solution of 1-[methyl-(2-pyrrolidin-1-yl-cyclohexyl)-carbamoyl]-2,3- diphenyl-cycloprop-2-enecarboxylic acid methyl ester (0.64 g, 1.26 mmol) in dichloromethane (3 cm$^3$) was added to lithium hydroxide monohydrate (0.265 g, 6.3 mmol) in a mixture of methanol (9 cm$^3$) and water (6 cm$^3$). The mixture was heated to reflux overnight. After cooling to room temperature, the solvents were evaporated and the residue partitioned between water (20 cm$^3$) and dichloromethane (20 cm$^3$). The organics were extracted with aqueous sodium hydroxide (20 cm$^3$) and the combined organics washed with dichloromethane (20 cm$^3$) before being acidified to pH =1 with dilute hydrochloric acid and extracted with dichloromethane (3×40 cm$^3$). The combined acidic extracts were dried, evaporated, and chromatographed (SiO$_2$, 5% to 10% methanol in dichloromethane) to separate the amino acid hydrochloride 0.17 g, 26%; mp 187–189° C.

$v_{max}$/cm$^{-1}$ 2940 (C—H), 1634 (NC=O), and 2594 (OC=O).

$R_f$=0.22 (SiO$_2$, 10% methanol in dichloromethane). Analysis for $C_{28}H_{32}N_2O_3$.(HCl)$_{1.5}$.H$_2$O: Requires: C, 65.02; H, 6.87; N, 5.42. Found: C, 65.09; H, 6.69; N, 5.20.

$^1$HNMR (400 mHz, CDCl$_3$): 7.94–7.45 (4H, m), 7.44–7.23 (6H, m), 4.70 (H, br s), 3.50–3.00 (5H, br s), 3.15 (3H, s, NCH$_3$), 1.87–1.66 (8H, m), and 1.33–1.19 (4H, m).

99% by HPLC; retention time =14.67 minutes (20% to 80% MeCN in H$_2$O +1% TFA over 20 minutes).

We claim:
1. A compound of formula

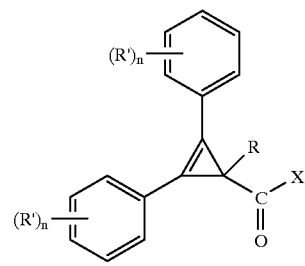

I or a pharmaceutically acceptable salt thereof wherein

X is

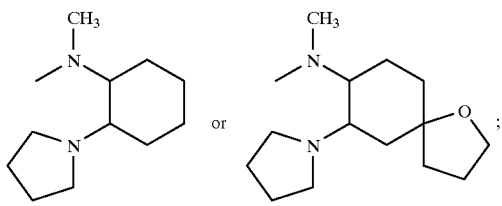

n is an integer of from 0 to 4; and
R' is halogen, $CF_3$, $NO_2$, $OR^2$, $CONR^3R^4$, or $NHCOCH_3$ wherein $R^2$, $R^3$, and $R^4$ are each independently selected from hydrogen and ethyl of from 1 to 6 carbons; and
R is hydrogen, COOH, or $COOCH_3$.

2. A compound named:
2,3-Diphenyl-cycloprop-2-enecarboxylic acid methyl-(2-pyrrolidin-1-yl-cyclohexyl)-amide;
2,3-Diphenyl-cycloprop-2-enecarboxylic acid methyl-(7-pyrrolidin-1-yl-1-oxa-spiro[4.5]dec-8-yl)-amide;
2-(3-Chlorophenyl)-3-phenyl-cycloprop-2-enecarboxylic acid methyl-(2-pyrrolidin-1-yl-cyclohexyl)-amide;
2-(4-Chlorophenyl)-3-phenyl-cycloprop-2-enecarboxylic acid methyl-(2-pyrrolidin-1-yl-cyclohexyl)-amide;
1-[Methyl-(2-pyrrolidin-1-yl-cyclohexyl)-carbamoyl]-2,3-diphenyl-cycloprop-2-enecarboxylic acid methyl ester; and
1-[Methyl-(2-pyrrolidin-1-yl-cyclohexyl)-carbamoyl]-2,3-diphenyl-cycloprop-2-enecarboxylic acid.

3. A method for treating stroke which comprises administering to a patient in need of said treatment a therapeutically effective amount of a compound in unit dosage form of claim 1.

4. A method for treating dystonia which comprises administering to a patient in need of said treatment a therapeutically effective amount of a compound in unit dosage form of claim 1.

5. A method for treating inflammatory disease which comprises administering to a patient in need of said treatment a therapeutically effective amount of a compound in unit dosage form of claim 1.

6. A method for treating pain which comprises administering to a patient in need of said treatment a therapeutically effective amount of a compound in unit dosage form of claim 1.

7. A method for treating cerebral ischemia which comprises administering to a patient in need of said treatment a therapeutically effective amount of a compound in unit dosage form of claim 1.

8. A method for treating diuresis which comprises administering to a patient in need of said treatment a therapeutically effective amount of a compound in unit dosage form of claim 1.

9. A method for treating asthma which comprises administering to a patient in need of said treatment a therapeutically effective amount of a compound in unit dosage form of claim 1.

10. A method for treating psoriasis which comprises administering to a patient in need of said treatment a therapeutically effective amount of a compound in unit dosage form of claim 1.

11. A method for treating irritable bowel syndrome which comprises administering to a patient in need of said treatment a therapeutically effective amount of a compound in unit dosage form of claim 1.

12. A pharmaceutical composition comprising a therapeutically effective amount of a compound according to claim 1 and a pharmaceutical acceptable carrier.

* * * * *